United States Patent [19]

Lo et al.

[11] Patent Number: 5,532,134
[45] Date of Patent: Jul. 2, 1996

[54] MYCOPLASMA DIAGNOSTIC ASSAY

[75] Inventors: Shyh-Ching Lo, Potomac; James W. K. Shih; Richard Y.-H. Wang, both of Bethesda, Md.

[73] Assignee: American Registry of Pathology, Washington, D.C.

[21] Appl. No.: 981,341

[22] Filed: Nov. 25, 1992

Related U.S. Application Data

[63] Continuation-in-part of Ser. No. 800,370, Dec. 2, 1991, Pat. No. 5,215,914, which is a continuation-in-part of Ser. No. 710,361, Jun. 6, 1991, Pat. No. 5,242,820, which is a continuation-in-part of Ser. No. 265,920, Nov. 2, 1988, abandoned, which is a continuation-in-part of Ser. No. 875,535, Jun. 18, 1986, abandoned.

[51] Int. Cl.$^6$ ................................................. G01N 33/53
[52] U.S. Cl. .................. 435/7.32; 435/7.2; 435/7.92; 435/870; 435/973; 435/253.1; 436/501; 530/389.5
[58] Field of Search .................... 435/253.1, 7.1, 435/7.2, 7.22, 7.32, 7.36, 7.92, 975, 870, 973; 436/501, 513, 518, 530; 530/389.1, 389.5

[56] References Cited

U.S. PATENT DOCUMENTS

| | | | |
|---|---|---|---|
| 4,855,227 | 8/1988 | McGarrity et al. | 435/7.32 |
| 5,084,561 | 1/1992 | Bredt et al. | 530/417 |

OTHER PUBLICATIONS

Chapter 30 "Serodiagnosis", pp. 505–512 in *Mycoplasmas Molecular Biology and Pathogenesis,* Maniloff et al, editors, (American Society for Microbiology, Washington, D.C., 1992).
Bricker et al, "Association of Lipids with Integral Membrane Surface Proteins of *Mycoplasma hyorhinis*", Infect. Immun. 56(2):295–301 (Feb. 1988).
Morrison–Plummer et al, "An ELISA to Detect Monoclonal Antibodies Specific for Lipid Determinants of *Mycoplasma pneumoniae*", J. Immunol. Methods, 64:165–178, (1983).
Lee et al, "Comparative Studies of Three Serologic Methods for the Measurement of *Mycoplasma pneumoniae* Antibodies", Am. J. Clin. Pathol., 92(3):342–347, (Sep. 1989).
Cimolai et al "Immunological Cross–Reactivity of a *Mycoplasma pneumoniae* Membrane–Associated Protein Antigen with *Mycoplasma genitalium* and *Acholeplasma laidlawii*", J. Clin. Microbiol., 25(11):2136–2139 (Nov. 1987).
Lo et al (1989)—Abstract Only—"Identification of *Mycoplasma incognitus* . . . " Am J Trop Med Hyg 41:601–616.
Hinshberg et al (1989)—Abstract Only—"Demonstration of Membrane Association . . . " J Gen Microbiol 135:613–621.
Stevens et al (1991) "Localization of the *M. pneumoniae* . . . " J. Bact 173:1041–1050.
Wang et al (1992) "High frequency Antibodies . . . " The Lancet 340:1312–1316.
Wise et al (1987)—Abstract Only—"Identification of Intrinsic and Extrinsic . . . ", Isr J Med Sci 23:469–473.
Riethman et al (1987) "Triton X–114 Phase Fractionation . . . " Infect. and Immun 55:1094–1100.
Wise et al (1987) "Major Membrane Surface Proteins . . . " J Bact. 169:5546–5555.
Boyer et al (1989) "Lipid–Modified Suface Protein . . . " Infect. and Immun. 57:245–254.

*Primary Examiner*—Carol A. Spiegel
*Attorney, Agent, or Firm*—Venable, Baetjer, Howard & Civiletti

[57] ABSTRACT

The present invention relates to a diagnostic assay utilizing the lipid associated membrane proteins of mycoplasmas to detect the presence of species-specific mycoplasma antibodies. The sensitive assay is useful for the detection and differentiation of mycoplasma antibodies specific for individual species in biological samples from humans and animals, and exhibits virtually no cross-reactivity between different mycoplasma species.

12 Claims, 7 Drawing Sheets

MYCOPLASMA DIAGNOSTIC ASSAY

RELATED DISCLOSURES

This is a continuation-in-part of U.S. patent application Ser. No. 07/800,370, filed Dec. 2, 1991, now U.S. Pat. No. 5,215,914 issued on Jun. 1, 1993, which is a continuation-in-part of U. S. patent application Ser. No. 07/710,361, filed Jun. 6, 1991, now U.S. Pat. No. 5,242,820, issued on Sept. 7, 1993, which is a continuation-in-part of U.S. patent application Ser. No. 265,920, filed Nov. 2, 1988, now abandoned, which is a continuation-in-part of U.S. patent application Ser. No. 875,535, filed Jun. 18, 1986, now abandoned.

BACKGROUND OF THE INVENTION

1. Field of the Invention

The present invention relates to a diagnostic assay for mycoplasma infections. The assay is based on antigen-antibody reaction and is effective in differentiating specific mycoplasma infection by species.

The ability to identify specific species of mycoplasma infection can be of great value. In addition to improving specific diagnosis, prognostication, knowledge of the particular mycoplasma species causing the infection allows the attending physician to select the most appropriate therapy for the individual patient, e.g. highly aggressive or less aggressive therapy regimens. Different species of mycoplasma often show different sensitivity to various antibiotics. Because of patient distress caused by more aggressive therapy regimens, it is desirable to distinguish those patients requiring such therapies.

Mycoplasma is a genus of cell wall-less sterol-requiring, catalase-negative pathogens commonly found in the respiratory and urogenital tracts of man and other animals. The cells of Mycoplasma are typically non-motile and pleomorphic, ranging from spherical, ovoid or pear-shaped to branched filamentous forms. Filaments are the typical forms in young cultures under optimal conditions, which subsequently transform into chains of coccoid cells which later break up into individual cells that are capable of passing through membrane filters of pore size 0.45 µm or even 0.22 µm.

A trilaminar cytoplasmic membrane contains sterols, phospholipid and proteins. Therefore, the cells are generally susceptible to polyene antibiotics and to lysis by digitonin.

Replication of the Mycoplasma genome may precede cytoplasmic division resulting in multinucleate filaments before individual cells are delimited by constriction. Budding can also occur.

Most Mycoplasma species are facultatively anaerobic, and all known species are chemoorganotrophic. The fermentative species of Mycoplasma utilize sugars such as glucose, while non-fermentative species can hydrolyze arginine. Only a few species of mycoplasma can utilize both glucose and arginine to grow.

Known mycoplasmas may be grown on complex media, such as Hayflick medium, while fastidious mycoplasmas may be grown on diphasic SP-4 medium. The colonies are usually of the "fried egg" type, i.e., an opaque, granular central region, embedded in the agar, surrounded by non-granular surface growth. The optimal growth temperature of mammalian strains is 36°–37° C.

Many species of Mycoplasma produce weak or clear hemolysis which appears to be due to the secretion of $H_2O_2$. This $H_2O_2$ secretion is believed to be responsible for some aspects of the mycoplasmas' pathogenicity. Known mycoplasmas are commonly sensitive to chloramphenicol and tetracyclines.

The Mycoplasma genus currently consists of more than 60 known species which are differentiated on the basis of various tests, including utilization of glucose and mannose, arginine hydrolysis, phosphatase production, the "film and spots" reaction and haemadsorption.

Mycoplasmas are the smallest and simplest free-living organisms known. Mycoplasmas are not obligatory intracellular microorganisms and are usually found extracellularly, but can be found intracellularly in the infected tissues (Mycoplasma, Eds. Wolfgang, J. J., Willette, H. P., Amos, D. B., Wilfert, C. M., *Zinsser Microbiology* 19th Ed. 1988, Appleton and Lange, 617–623). The term mycoplasma apparently was first used by B. Frank in 1889 (Frank B., *Dent. Bot. Ges.*, 7, 332 (1889) and Krass, C. J. et al., *Int. J. Syst. Bacteriol.* 23, 62 (1973)). Frank, after careful microscopic observation, began writing about invasion of plants (legume) by these microorganisms and stated: "the changed character of the protoplasm in the cortical cells arising from infection, I will designate as mycoplasma". Later, he had more explicitly defined mycoplasma as a mixture of small fungus-like microorganisms and cell protoplasm (Frank, B., *Landwirt. Jahrb.* 19, 523 (1890)). The description reflected the difficulty of differentiating this unique microorganism from the infected host cells morphologically.

Even today with electron microscopy, it is still often difficult to differentiate the mycoplasmas from the cellular protoplasmic processes or the subcellular organelles of the infected host, because ultrastructurally, these have microorganisms have protoplasm-like internal structures and are bounded by only an outer limited membrane (unit membrane) without a cell wall. Thus, there have been few electron microscopic studies of mycoplasmas identified directly in the infected tissues of animals or humans.

It has been reported that ultrastructural examination of infected tissues has failed to localize the microbe, even in tissues where very high titers ($>10^9$/gm) of microorganisms were recovered in culture (Elizan, T. S. et al., *Pro. Soc. Exp. Biol. Med.* 139, 52 (1972) and Schwartz, J. et al., *Pro. Soc. Exp. Biol. Med.* 139, 56 (1972)). Therefore, morphologically, the microbe might be mimicking certain normal cellular or subcellular structures in the infected host tissues and preventing direct identification.

In addition to the natural difficulty of morphological differentiation between the microorganisms and the protoplasm of infected cells, the often poorly preserved formalin-fixed clinical materials present further limitations to any attempt to directly visualize mycoplasma organisms in the tissues.

Mycoplasmas cause a variety of diseases in animals, plants and insects. However, the roles of known human mycoplasmas except for *M. pneumoniae* in causing atypical pneumonia are difficult to assess. Urines or urogenital swabs from healthy people and patients with a variety of different diseases have already been examined extensively. *U. urealyticum* and *M. hominis* were the most commonly found mycoplasmas. Taylor-Robinson, D., et al., *Nature* 222, 274 (1969); Tarr, P. I., et al., *J. Infec. Dis* 133, 419 (1976); Taylor-Robinson, D., et al., *N. Eng. J. Med.* 302, 1003 (1980); Fiacco, V., et al., *J. Clin. Microbiol.* 20, 862 (1984). Although a wide variety of urogenital and reproductive disorders have been associated with *U. urealyticum* and *M. hominis*, it has been difficult to establish a definite etiological role for them because they are often found as frequently in patients without disease as in those with disease. Taylor-Robinson, D., et al., *N. Eng. J. Med.* 302, 1003 (1980). *M. genitalium* was also isolated from two patients with non-gonococcal urethritis. However, most patients with urogenital diseases do not have clear evidence of *M. genitalium* infection. Tully, J. G., et al., *Lancet* 1, 1288 (1981). On the other hand, mycoplasmas are known to be extraordinary pathogens, capable of causing chronic debilitating diseases and producing a variety of clinical manifestations in animals and frequently suppressing host immune defense mechanisms. *The Mycoplasmas*, Vol. IV, Razin, S., Barile, M. F., eds., Academic Press, pp. 203–286 (1983).

2. Description of the Background Art

As noted above, mycoplasmas are currently differentiated by various tests for their unique biological and biochemical properties including utilization of glucose and mannose, arginine hydrolysis, phosphatase production, the "film and spots" reaction and haemadsorption. Classical serologic tests for detection of antibodies to either whole organisms or purified fractions include: indirect fluorescent antibodies (whole organisms), complement fixation, passive hemagglutination, agglutination, growth inhibition on agar and metabolic inhibition in broth medium. Also, an immunochemical assay for *Mycoplasma genitalium* using specific monoclonal antibodies in sandwich ELISA binding assay has been claimed in U.S. Pat. No. 5,158,870. However, a sensitive and specific assay detecting antibodies to each specific species of mycoplasma is still urgently needed in the clinics.

At least part of the reason for the lack of such an immunological assay is the significant cross reactions of mycoplasma proteins between different species of mycoplasma, as well as the reported tendency of mycoplasmas to rapidly alter expression and structure of their lipid-modified, cell-surface proteins. Rosengarten, R. and Wise, K., *Science* 247, 315 (1990). In fact, differences in the expression (phase variation) and in size of lipid-modified, integral membrane protein antigens at the cell surface have been reported among progenies from a single mycoplasma organism, and render development of a serological assay to the ever changing lipid-modified integral membrane protein antigen unlikely. Id. Thus, an accurate immunological diagnostic assay to detect mycoplasma infections and to specifically distinguish between different species of mycoplasma would represent a significant advancement in the art.

SUMMARY OF THE INVENTION

The present invention relates to a diagnostic assay utilizing a specific group of surface antigens, the lipid-associated membrane proteins (LAMP) of mycoplasmas, to detect the presence of species-specific mycoplasma antibodies. The LAMP of mycoplasmas are highly antigenic, and thus, capable of inducing good antibody responses in the infected hosts. The antibody assay exhibits virtually no cross-reactivity between different mycoplasma species, and is the first diagnostic assay to use LAMP for such a purpose. The assay is useful for the detection of species-specific antibodies to mycoplasmas in biological samples from humans and animals.

BRIEF DESCRIPTION OF THE DRAWINGS

The various aspects, advantages, and novel features of the present invention will be more clearly understood from the following detailed description when read in conjunction with the appended figures, in which.

DETAILED DESCRIPTION OF THE INVENTION

The present invention relates to an immunologically based diagnostic assay which detects and distinguishes infections of mycoplasmas by specific species. The assay utilizes LAMP, which is a group of surface proteins in mycoplasmas found to be antigenically different between species.

Contrary to the teachings of the art, the present inventors have found that LAMP from all mycoplasma species is highly antigenic and species-specific, and thus useful for detecting and differentiating polyclonal mycoplasma specific antibodies in biological samples, including sera, plasma and body fluids. The differentiation which is achieved by detecting species-specific mycoplasma antibodies permits the identification of infection by a specific species of mycoplasma in human and animal hosts.

In order to isolate LAMP, log-phase mycoplasma are pelleted, washed in 4° C. phosphate-buffered saline (PBS) pH 7.2 and stored at −70° C. The pellets are then briefly sonicated at 4° C. in buffer A (50 mM Tris-HCl pH 8.0, 150 mM NaCl, 1 mM EDTA) adjusted to 1 mg/ml protein in buffer A, solubilized by adding TRITON®X-114 (TRITON® X-114 is also called TX-114 and is a mix of polyoxyethylene ethers and other surface active compounds). (TX-114, Boehringer, diluted to 10% (v/v) with sterile deionized water) to a final concentration of 2% TX-114 (v/v) incubated at 4° C. for one hour, salinized with NaCl to 0.5M and reincubated at 4° C. for 90 minutes. The lysate is then centrifuged at 5° C. for 20 minutes at 20,840

× g. For each phase fractionation, supernatant in a new tube is incubated at 37° C. for 5 minutes to induce condensation of TX-114, and centrifuged at 30° C. for 5 minutes at 8,100 × g. The resulting heavy TX-114 phase is saved, readjusted to original volume with 4° C. buffer A, vortexed, iced at 4° C. for 10 minutes, and the procedure for phase fractionation is repeated for two more cycles. Then, the final TX-114 phase is resuspended in 4° C. buffer A to the original volume, and centrifuged at 5° C. for 20 minutes at 20,840 × g to remove insoluble materials. The supernatant is saved, designated as TX-114 extract, and may be used as the antigen for enzyme-linked immunosorbent assay (ELISA) and western blots.

In the ELISA for antibodies to LAMP antigens, TX-114 extract, diluted in 20 mM NaHCO$_3$ buffer, pH 9.6, 0.15M NaCl to a protein concentration of about 2 mg/ml, is coated on plates at 37° C. for 4 hours with 100 µl in each well, overcoated with 0.1% bovine serum albumin (BSA) plus 0.02% sodium azide at 25° C. for two hours, and washed twice with solution A (PBS pH 7.2 plus 0.05% NON-IDENT® P-40 (NONIDENT® P-40 is also called NP-40 and is an octylphenol-ethylene oxide condensate containing an average of 9 moles ethylene oxide per mole of phenol). Then, 100 ul of human serum or plasma, diluted 1:250 in 10% normal goat serum, 2% BSA, and 0.3% NP-40 in PBS is added to each well and incubated at 5° C. overnight, then at 37° C. for 90 minutes. Excess liquid is aspirated to stop the reaction and the plates are washed six times with solution A. Each well received 100 ul of 1:1000 biotin-labeled antibody of goat anti-human IgG gamma in diluent I (10% normal goat serum, 2% BSA, 0.1% NP-40 in PBS), is incubated at 37° C. for 90 minutes, washed as described above, incubated with 1:20,000 peroxidase-labelled strepavidin in diluent I at 37° C. for 90 minutes, washed as described above, developed with 100 ul of ABTS peroxidase substrate solution at 37° C. for 20 minutes, and the reaction stopped by adding 100 ul 1% sodium dodecylsulphate (SDS) solution.

The optical density (OD) of each well at 405 nm corrected with a reference wavelength at 650 nm is measured with a microtitre plate reader with automatic subtraction of the OD of the blank. Absorbance readings greater than the mean reading of mycoplasma normal subjects plus 4 standard deviations are considered to be positive for mycoplasma antibodies.

Figure 1:
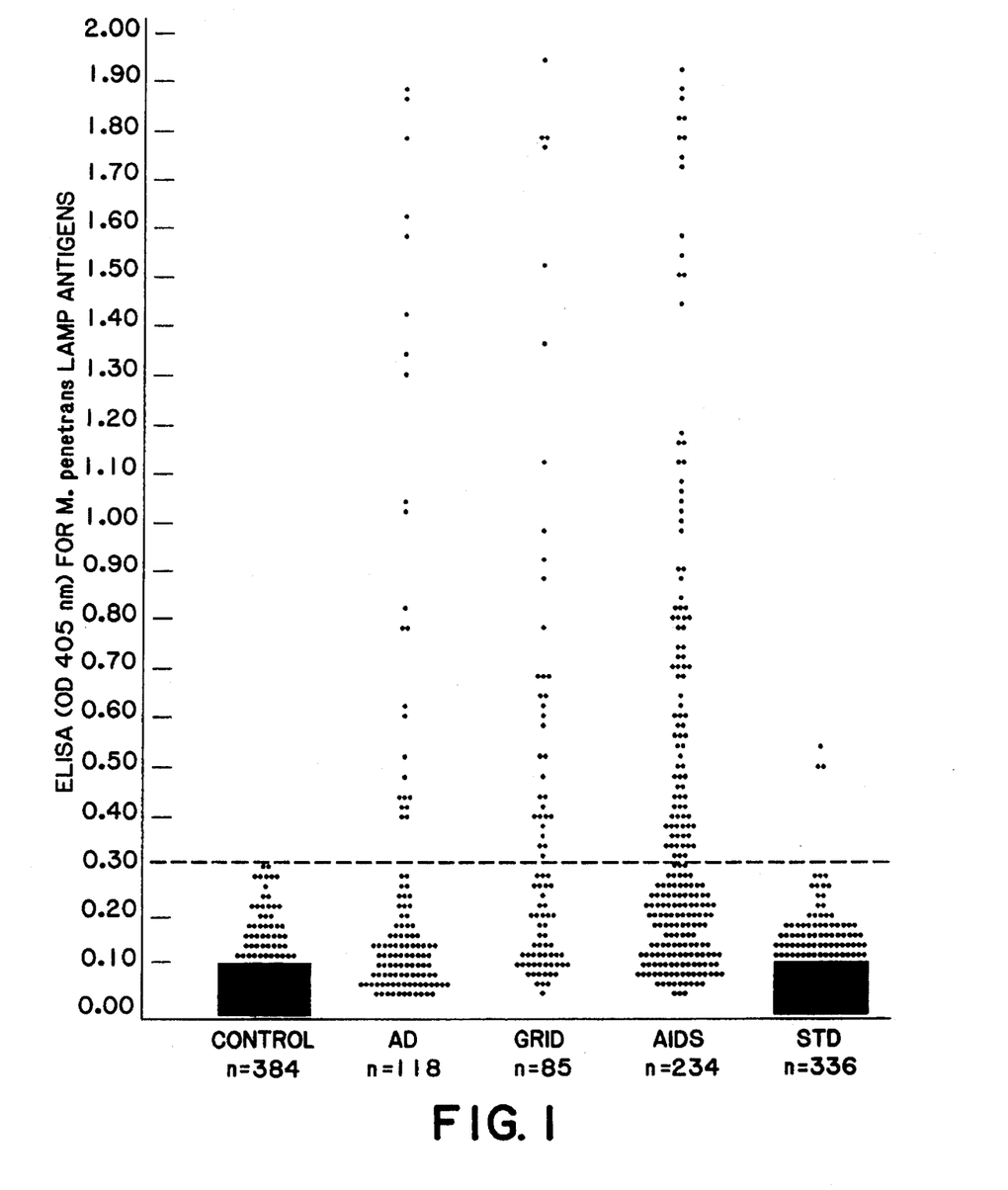
FIG. 1 graphically depicts a comparison of immune reactivity of *M. penetrans* LAMP antigens by ELISA in serum samples from HIV$^-$donors (AD), patients who died of "gay-related infectious disease" (GRID), patients with AIDS (AIDS), and patients attending sexually transmitted disease (STD) clinics.

A comparison of immune reactivity of *M. penetrans* LAMP antigens by ELISA is shown in FIG. 1 in which serum samples from HIV$^-$normal blood donors (control), asymptomatic HIV$^+$donors (AD), patients who died of "gay-related infectious disease" (GRID), patients who had AIDS (AIDS), and patients attending sexually transmitted disease (STD) clinics were used. The number of sera tested in each group is indicated as "n=". The OD reading of 0.3 (mean value plus 4 standard deviations (SD) from 383 normal blood donors) was the cutoff line for this ELISA test. Each sample was tested at least twice. All positive samples were repeated three times and were also tested in plates coated with BSA without mycoplasmal antigens to rule out non-specific binding problems. The black blocks (OD ≦0.10) represent 330 dots (86%) and 255 dots (76%) of samples from HIV$^-$blood donors and STD clinics patients, respectively.

Figure 2:
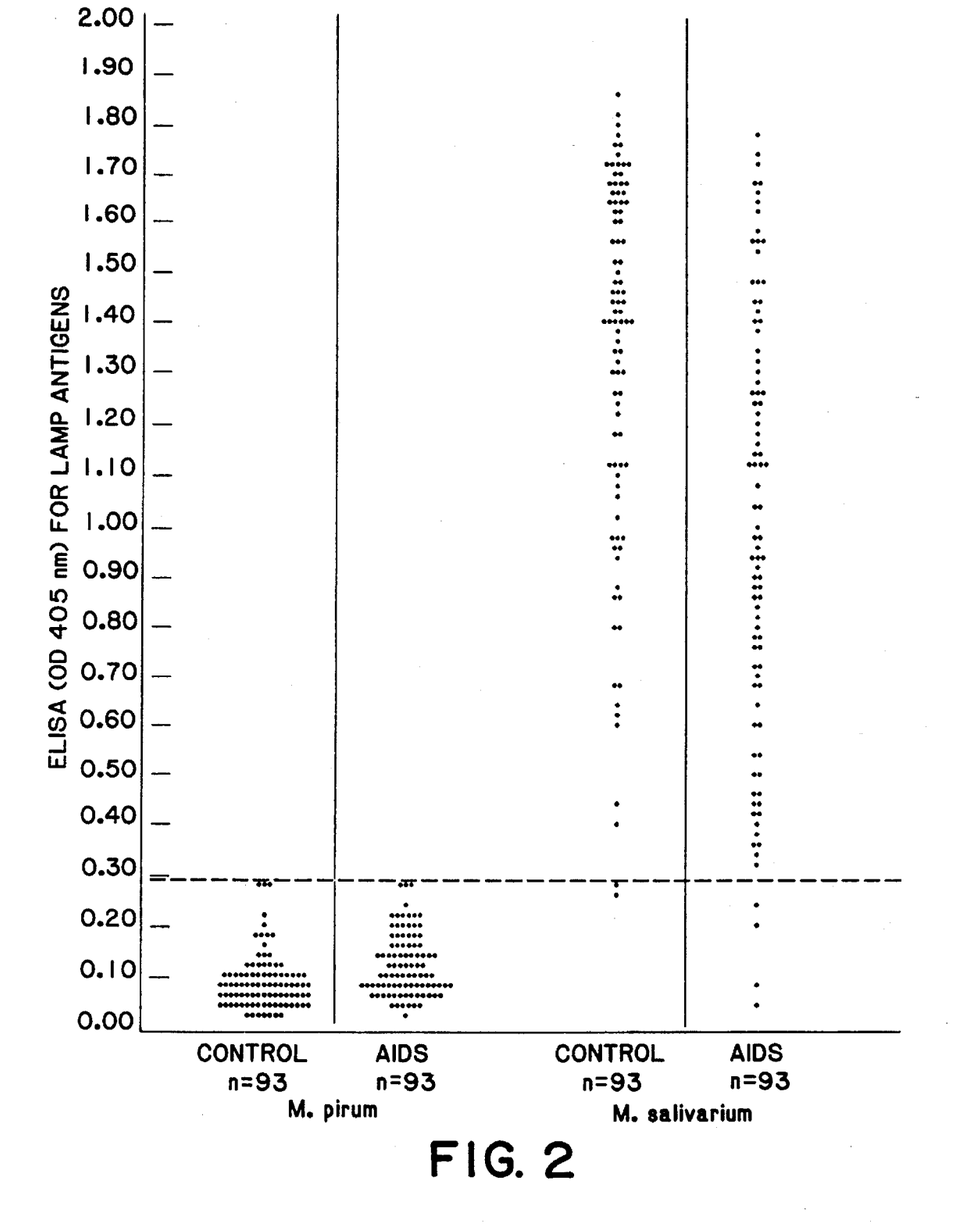
FIG. 2 graphically depicts a comparison of antibodies to *M. pirum* LAMP and *M. salivarium* LAMP in serum samples from control subjects and from patients with AIDS.

Similarly, FIG. 2 shows a comparison of antibodies to *M. pirum* and *M. salivarium* LAMP antigens by ELISA in serum samples from control subjects and from patients with AIDS. The preparation of mycoplasmal surface antigens and enzyme immunoassays were performed using the same methods described for *M. penetrans*. The sum of the mean value plus the value of 4 SD for sera reacting with *M. pirum* from 93 HIV normal blood donors (0.296) was considered to be the cut-off for a positive result. The immune reactivity of *M. pirum* LAMP on ELISA plates was confirmed by testing with hyperimmunized rabbit antiserum which gave OD readings greater than 1.7 at 1:10000 dilution.

Figure 4:
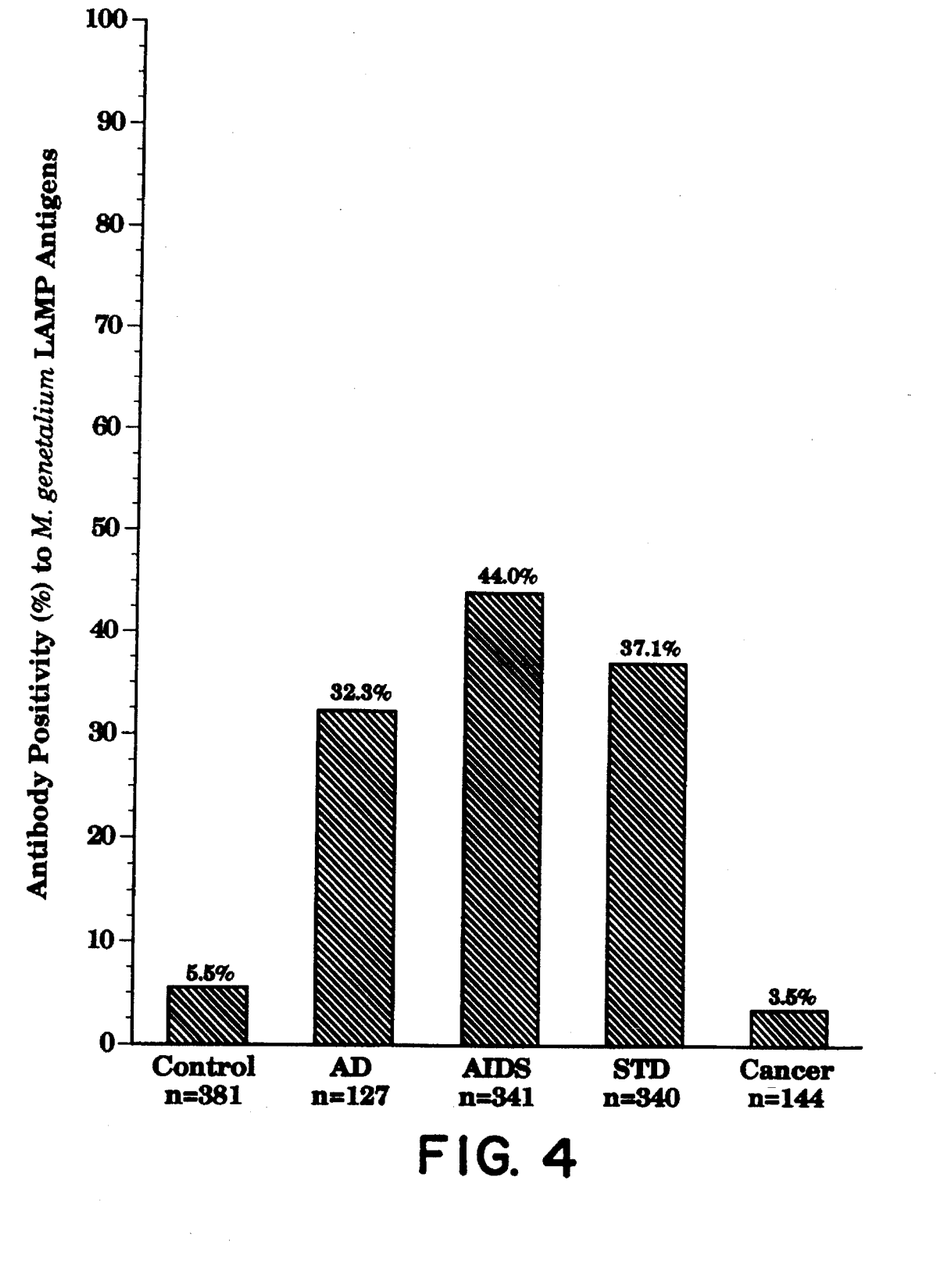
FIG. 4 graphically depicts the positive frequency of antibodies to *M. genitalium* LAMP antigens by ELISA. In the figure, Control represents HIV-negative healthy blood donors, AD represents asymptomatic HIV-infected blood donors, AIDS represents HIV$^+$patients with AIDS, STD represents patients attending sexually transmitted disease clinics, Cancer represents patients with malignant diseases (63 with various neoplasms, 81 with malignant lymphoma).
Figure 6:
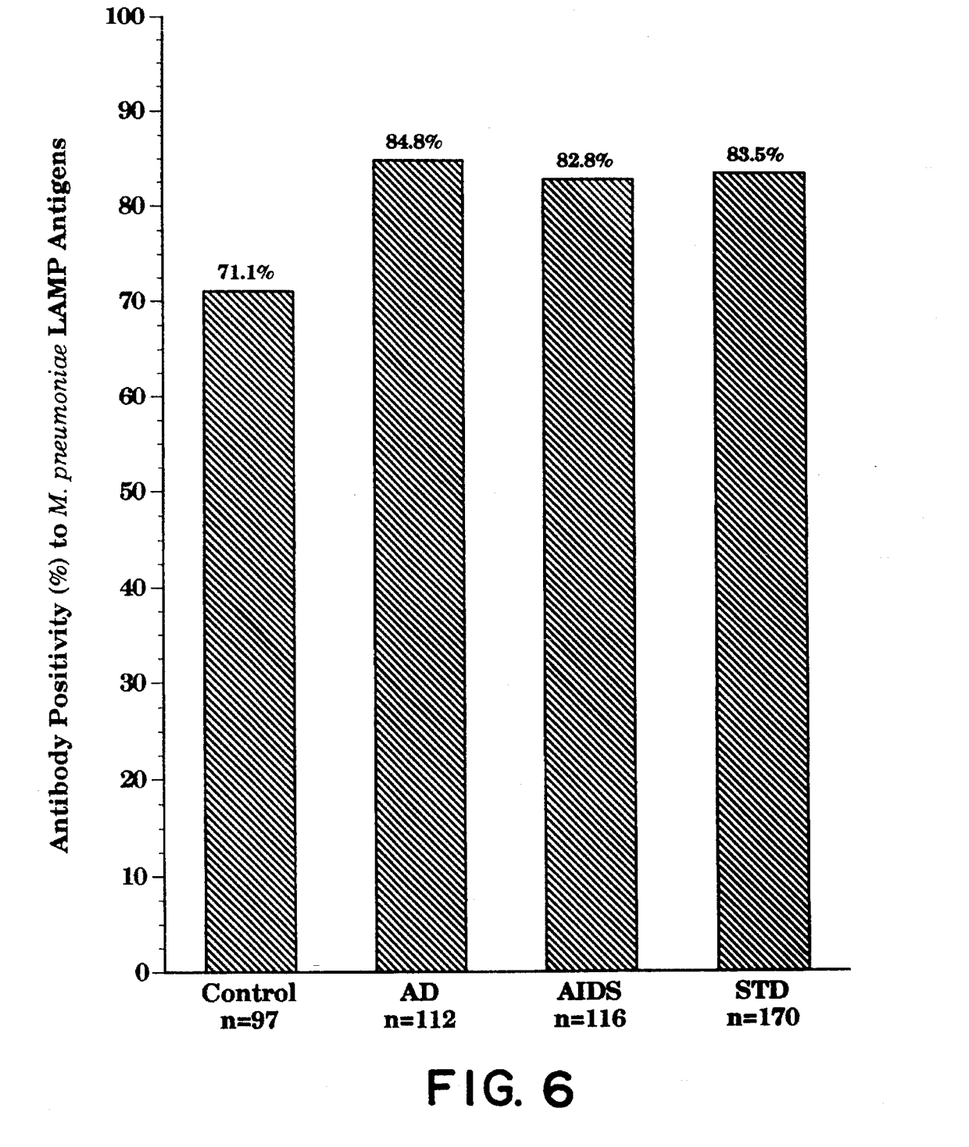
FIG. 6 graphically depicts the positive frequency for antibodies to *M. pneumoniae* LAMP antigens in ELISA. Control represents HIV-negative healthy blood donors, AD represents asymptomatic HIV-infected blood donors. AIDS represents HIV$^+$patients with AIDS, STD represents patients attending sexually transmitted disease clinics.

Also FIGS. 4 and 6 show the positive frequency of antibodies to *M. genitalium* and *M. pneumoniae* LAMP antigens, respectively, by ELISA. In FIG. 4, Control represents HIV-negative healthy blood donors, AD represents asymptomatic HIV-infected blood donors, AIDS represents HIV$^+$patients with AIDS, STD represents patients attending sexually transmitted disease clinics, and Cancer represents patients with malignant diseases (63 with various neoplasms, 81 with malignant lymphoma). The sum of the mean value plus 4 SD for sera from the control subjects was used as the cut-off for positivity. In FIG. 6, Control represents HIV-negative healthy blood donors, AD represents asymptomatic HIV-infected blood donors, AIDS represents HIV$^+$ patients with AIDS, and STD represents patients attending sexually transmitted disease clinics. The cut-off value for positivity in ELISA was 0.45.

In western blotting, proteins from mycoplasma Tx-114 extract are separated by SDS-polyacrylamide gel electrophoresis and electroblotted on a nitrocellulose membrane. The membrane is blocked with 5% fetal bovine serum and 1% BSA in PBS pH 7.2 and cut into strips. Each strip is preincubated for 5 minutes with 2 ml diluent I and 0.02% sodium azide, 1:250 dilution human serum added, and incubated at 25° C. for 15 hours with shaking. These strips are washed six times with solution A, incubated at 25° C. with 1:1000 biotin-labelled antibody of goat anti-human IgG gamma, incubated at 25° C. with 1:10,000 peroxidase-labelled streptavidin in diluent I, and developed at 37° C. for 20 minutes with 4-chloro-1-naphthol peroxidase substrate system.

Figure 3:
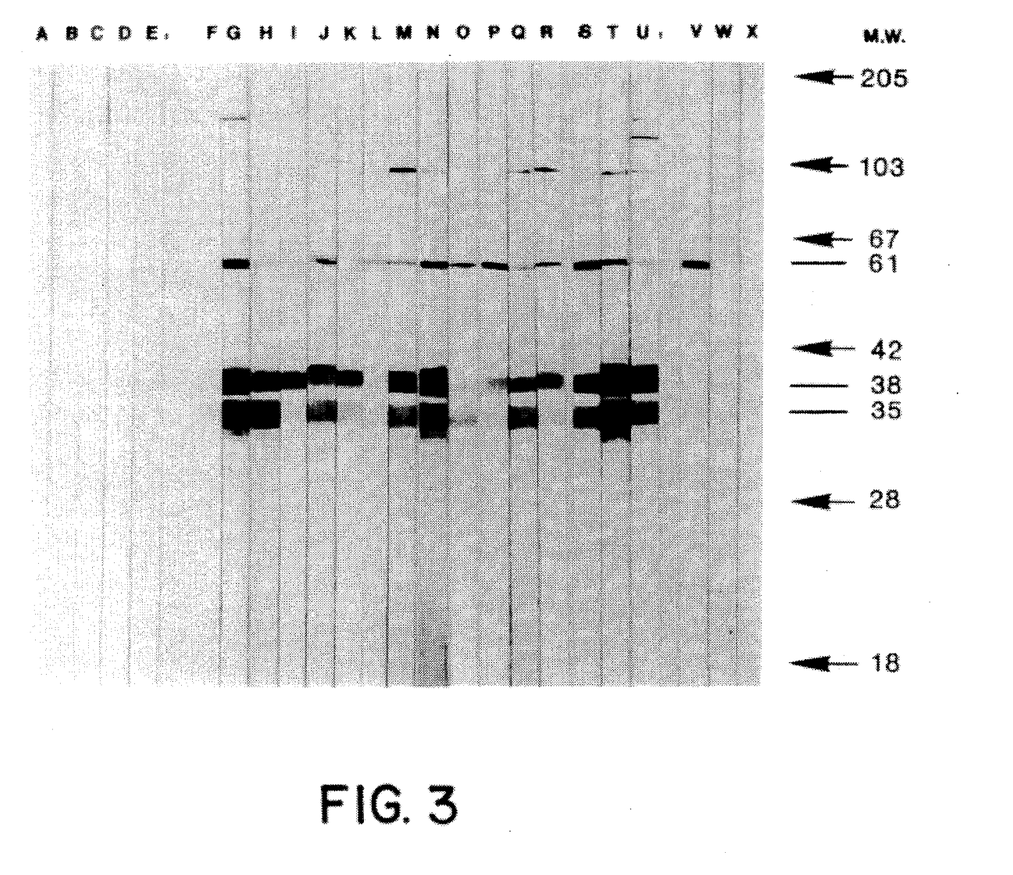
FIG. 3 shows a western blot analysis of human immune reactivity of *M. penetrans* LAMP antigens with sera and plasma.

A western blot analysis of human immune reactivity of *M. penetrans* LAMP antigens is shown in FIG. 3. Lanes A–E show sera from 5 HIV$^-$healthy blood donors. Lanes F–U show sera or plasmas from 16 HIV$^+$individuals with a positive ELISA test to *M. penetrans* antigens; lanes F–K, patients from AD group; lanes L–R, patients from AIDS groups; lanes S–U, patients from GRID group. Lanes V–X show AIDS patients with a negative ELISA test to *M. penetrans* antigens. The arrows indicate the positions of prestained protein size markers with apparent molecular weight from top to bottom of 205 kd (kilodalton), 103 kd, 67 kd, 42 kd, 28 kd, and 18 kd, respectively.

Figure 5:
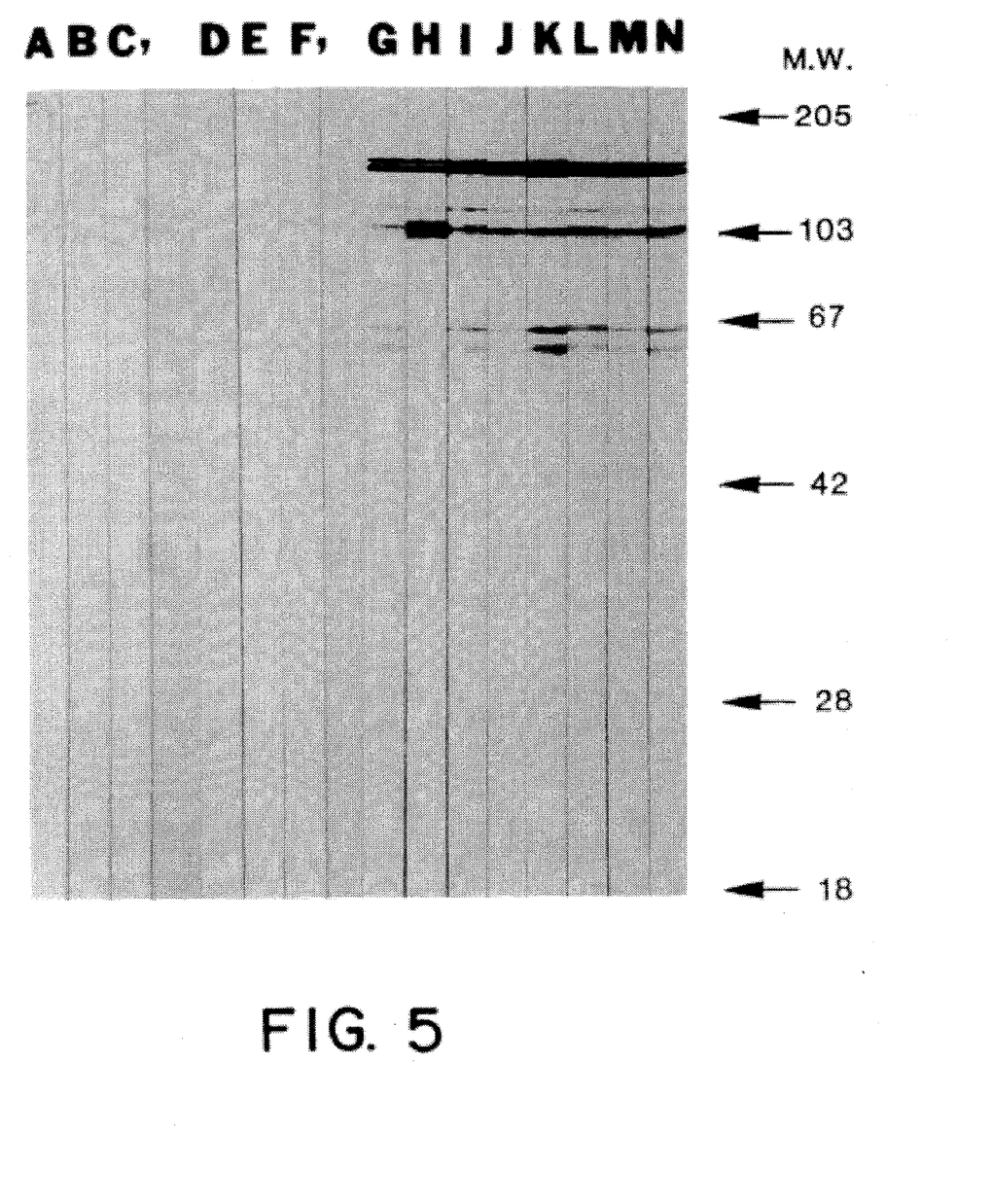
FIG. 5 shows a western blot analysis of antibody reactivity to *M. genitalium* LAMP antigens with human sera and plasma.
Figure 7:
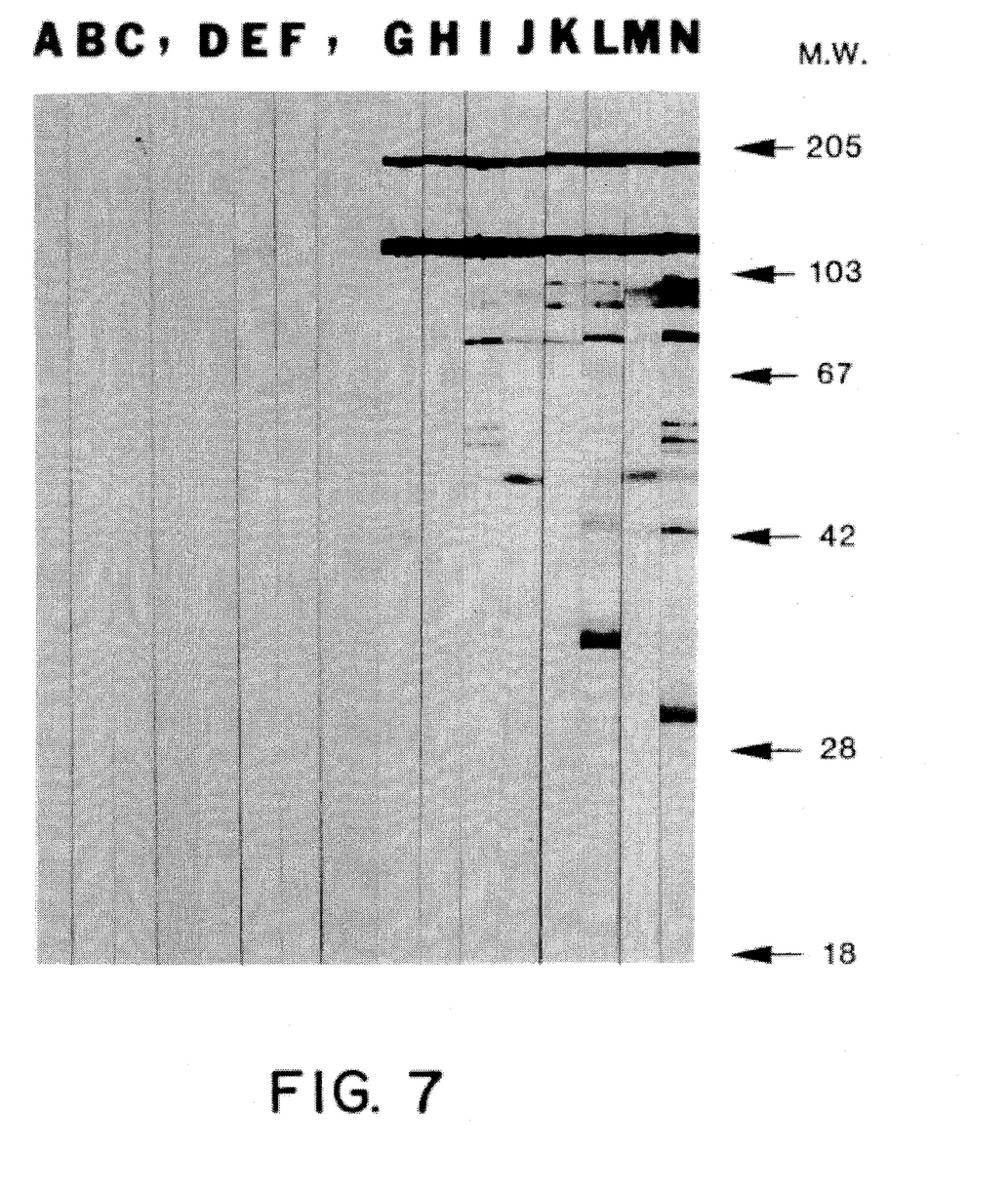
FIG. 7 shows a western blot analysis for antibody reactivity to *M. genitalium* LAMP antigens with human sera and plasma.

Similar western blot analyses of human immune reactivity of *M. genitalium* and *M. pneumoniae* LAMP antigens are shown in FIGS. 5 and 7, respectively. In FIG. 5, lanes A–C show sera from 3 HIV-negative healthy blood donors; lanes D–F show sera from 3 HIV-negative individuals having positive reactivity to *M. pneumoniae* but negative reactivity to *M. genitalium* in ELISA; lanes G–N show sera from HIV-infected patients (G to K) and HIV-negative patients attending STD clinics (L to N) having positive reactivity to *M. genitalium* in ELISA. The arrows indicate the position of prestained protein size markers with apparent molecular weight from top to bottom of 205 kd (kilodalton), 103 kd, 67 kd, 42 kd, 28 kd, and 18 kd, respectively. In FIG. 7, lanes A–F show sera from 6 HIV-negative individuals; lanes A–C show sera from individuals found to be negative for both *M. pneumoniae* and *M. genitalium* antibodies in ELISA; lanes D–F show sera from 3 patients attending STD clinics having positive reactivity to *M. genitalium* but negative reactivity to M. pneumoniae in ELISA; lanes G–J show sera from HIV-negative healthy blood donors having negative reactivity to M. genitalium but positive reactivity to M. pneumoniae in ELISA; lanes K–N show sera from HIV-infected patients having positive reactivity to both M. genitalium and M. pneumoniae in ELISA. The arrows indicated the position of prestained protein size markers with apparent molecular weight from top to bottom of 205 kd (kilodalton), 103 kd, 67 kd, 42 kd, 28 kd, and 18 kd, respectively.

As presented in greater detail below in the Examples, a comparison of the western blots for the LAMP antigens derived from different species of mycoplasma following TX-114 treatment reveal different bands for each species of mycoplasma which can be used to identify and differentiate species-specific antibodies to various mycoplasmas. The western blots with LAMP produce very little interference or cross-reactivity between antibodies reacting to different species, and thus, clearly discernible separate bands for different mycoplasmas species are identifiable. The sensitivity and specificity of diagnostic assay using LAMP are also shown in the Examples of ELISA.

The species specificity of the present assay using LAMP has been demonstrated by testing the cross-reactivity of LAMP from M. penetrans with polyclonal antibody to a variety of other mycoplasma species. Particulary, polyclonal rabbit antibody raised against each of the human mycoplasmas, M. fermentans (incognitus strain and PG-18), M. pirum, M. pneumoniae, M. genitalium, M. orale, M. salivarium, M. hominis and Acholeplasma laidawii did not react with M. penetrans in a dot-blot immunochemical assay or an immunofluorescence assay. Conversely, rabbit antiserum raised against M. penetrans LAMP antigens failed to react with these mycoplasmas in the same assays.

A diagnostic kit for the detection and differentiation of mycoplasmas species-specific antibodies can be prepared in a conventional manner using the LAMP of each different mycoplasma species to be identified. The assays performed with these kits, will provide specific and sensitive results, particularly, very little if any cross-reactivity between antibodies to different mycoplasma species. The assays are highly valuable for diagnosis of mycoplasma infection by a specific species in clinics.

The present invention is further illustrated by reference to the following examples. These examples of measuring antibodies to specific species of mycoplasma are provided for illustrative purposes, and are in no way intended to limit the scope of the invention.

EXAMPLE 1

Isolation of M. penetrans

All the urine specimens from HIV$^+$patients in this study were collected in two AIDS clinics. Urine specimens from 38 HIV$^+$patients were first obtained from clinic I. Later, urine specimens from 75 HIV$^+$patients were obtained from a second clinic (clinic II) located in different geographic region over a period of 3 months. The 98 control urine specimens were obtained from age-matched HIV$^-$healthy donors. For the repeated isolations from the first clinic I patient with M. penetrans infection, the urine specimens were purposely coded at the site of collection to verify each isolation.

Urine was collected in sterile containers and concentrated 10-fold by centrifugation (3000×g for 15 minutes at 4° C.) and resuspended in 1/10 of the original urine. The resulting urine sediments were cultured after serial 1:10 dilutions in modified SP-4 media (Tully, J. G., et al., Science 195, 892 (1977); Lo, S-C., et al., Am. J. Trop. Med. Hyg. 41, 586 (1989)) (glucose 0.1% and arginine 0.01%) in 12×75 mm tissue culture tubes, incubated at 37° C. aerobically and in GasPak jars (BBL, Micro. Sys. Cockeysville, Md.) anaerobically, and observed daily for a change in color. Tubes showing color change were inoculated onto 60 mm petri dishes containing 5 ml of modified SP-4 agar (1%).

The mycoplasma from the initial patient at clinic I was triple cloned by passing a broth culture through 220 nm membrane filter, incubating the filtrate on SP-4 agar for 10–14 days at 37° C. and isolating a well formed single colony. This mycoplasma was also examined for possible bacterial reversion by passing the organism 5 times in antibiotic-free medium. The organism was then studied for cell wall formation under electron microscopy (E.M.) and also subcultured to conventional blood agar for bacterial colony examination after 72 hours at 37° C.

The urine sediments from one HIV$^+$male homosexual patient at clinic I grew M. penetrans with an estimated titer of $10^5$/ml urine. This patient was asymptomatic, without Kaposa sarcoma or any opportunistic infection, but did have persistant low $CD_4^+$lymphocyte counts ($<100\times10^6$/liter) during the previous two years. SP-4 broth cultures of the patient's urine sediments appeared slightly turbid, and the pH shifted markedly to acid after 8 to 10 days incubation. It was found that anaerobic conditions slightly improved growth of M. penetrans. M. penetrans was repeatedly isolated in high titers from the urines of this patient in all six subsequent attempts over four months. M. penetrans was also isolated from the urine of five other HIV$^+$patients from clinic II. The control urines from 98 HIV$^-$patients did not contain M. pentrans.

Detailed antigenic and DNA comparison between M. penetrans and other species of mycoplasmas showed M. penetrans is a previously unknown species of mycoplasma. However, other mycoplasma species including M. fermentans, M. orale, M. hominis, M. alvi, M. sualvi, M. iowae, M. moatsii, M. pirum, M. buccale, M. spermatophilum, M. pneumoniae, M. genitalium, M. salvarium, M. hominis, Acholeplasma laidwii and other mycoplasma are well-known in the art as are the techniques for their isolation.

EXAMPLE 2

Preparation of M, penetrans LAMP Antigens

M. penetrans, as isolated in Example 1 was prepared by pelleting logarithmic-phase cultures and washing twice with ice-cold phosphate-buffered saline (PBS), pH 7.2 (Biofluids, Inc., Rockville, Md.). The cell pellets were stored at −70° C. before use. Triton X-114 (TX-114) was purchased from Boehringer Mannheim Corporation, Indianapolis, Ind. and diluted to 10% (vol./vol.) with sterile deionized water. Mycoplasmas were subjected to TX-114 phase partitioning by a modification of the method originally described by Bordier, J. Biol. Chem. 256, 1604 (1981) (incorporated herein by reference) which was subsequently adapted to mycoplasmas described by Wise, K. S. et al., J. Bacteriol. 169, 5546 (1987) (incorporated herein by reference). The cell pellets were resuspended by brief sonication in ice-cold 50 mM Tris-HCl, pH 8.0, 150 mM NaCl, 1 mM EDTA (buffer A), and adjusted to a protein concentration of 1 mg/ml. The cells were solubilized by adding TX-114 to a final concentration of 2% (v/v), incubating in ice for 1 hour with occasional mixing, and continuing incubation for another 90 minutes after addition of NaCl to a final concentration of 0.5 M. The lysates were centrifuged at 5° C. for 20 minutes at 20,840×g. The supernatant was collected and transferred to a new tube, incubated in a 37° C. water bath for 5 minutes to induce condensation of TX-114, and then centrifuged at 30° C. for 5 minutes at 8,100×g. The resulting heavy, detergent-enriched fraction (TX-114 phase, about one tenth original total volume) was saved and readjusted to the original volume with ice-cold 50 mM Tris HCl, pH 8.0, 0.5 M NaCl, 1 mM EDTA. The solution was thoroughly mixed by vortexing, left in ice for 10 minutes, and then repartitioned as described above. In the third cycle of phase fractionation, the condensed TX-114 phase was resuspended in buffer A and processed as described above. The final condensed TX-114 extract was resuspended with ice-cold buffer A to the original volume, and clarified by centrifugation at 5° C. for 20 minutes at 20,840× g to remove insoluble materials. The supernatant was saved, designated as TX-114 extract, and used as antigens for ELISA and Western blot analyses described in Examples 3 through 9 below.

These same techniques have been used to prepare LAMP antigens of *M. fermentans, M. orale, M. pirum, M. pneumoniae, M. genitalium, M. salivarium, M. hominis* and *Acholeplasma laidawii,* and can be used to prepare LAMP antigens of other mycoplasma species including *M. hyorhinis, M. alvi, M. sualvi, M. iowae, M. moatsii, M. buccale* and *M. spermatophilum.*

EXAMPLE 3

Western Blot with *M. penetrans* LAMP Antigen

*M. penetrans* LAMPs (about 90 μg) from the TX-114 extract of Example 2 were separated by SDS-PAGE on a 10% gel (12×12 cm separating gel, 0.75 mm thickness), and electroblotted on a BA-85 nitrocellulose membrane (Schleicher & Schuell Inc., Keene, N.H.). The membrane was blocked with 5% fetal bovine serum, 1% BSA in phosphate-buffered saline (PBS), pH 7.2, for 30 minutes, air dried, and cut into 4 mm strips. Each strip was preincubated for 5 minutes with 2 ml diluent containing 10% normal goat serum, 2% BSA, 0.1% NP-40, in PBS (diluent I), and 0.02% sodium azide, then serum was added at a dilution of 1:250. The reaction was carried out at 25° C. for 15 hours with continuous shaking, and then stopped by aspirating the fluid and washing the strips 6 times with 0.05% NP-40 in PBS. Followed by incubation with 1:1,000 diluted biotin-labeled antibody of goat anti-human IgG (r) and subsequent incubation with 1:10,000 diluted peroxidase-labeled streptavidin in diluent I for 2 hours each at 25° C., the strips were developed at 37° C. for 20 minutes with 4-chloro-1-naphthol peroxidase substrate system (Kirkegaard Perry Laboratories, Inc., Gaithersburg, Md.).

FIG. 3 shows the results of this analysis in which lanes A–E are sera from 5 HIV⁻healthy blood donors, lanes F–U are sera or plasmas from 16 HIV⁺individuals with a positive ELISA test to *M. penetrans* antigens; lanes F–K, patients from AD group; lanes L–R, patients from AIDS groups; lanes S–U, patients from GRID group, and lanes V–X are AIDS patients with a negative ELISA test to *M. penetrans* antigens. The arrows indicate the positions of prestained protein size markers with apparent molecular weight from top to bottom of 205 kd (kilodalton), 103 kd, 67 kd, 42 kd, 28 kd, and 18 kd, respectively.

EXAMPLE 4

Western Blot with *M. pneumoniae* LAMP Antigen

*M. pneumoniae* LAMPs (about 90 μg) prepared using the procedures taught in Example 2 were subjected to western blot analysis as taught in Example 3. The results of this analysis are shown in FIG. 7 wherein lanes A–F are sera from 6 HIV-negative individuals; lanes A–C from individuals found to be negative for both *M. pneumoniae* and *M. genitalium* antibodies in ELISA, and lanes D–F from 3 patients attending STD clinics having positive reactivity to *M. genitalium* but negative reactivity to *M. pneumoniae* in ELISA, lanes G–J are sera from HIV-negative healthy blood donors having negative reactivity to *M. genitalium* but positive reactivity to *M. pneumoniae* in ELISA, and lanes K–N are sera from HIV-infected patients having positive reactivity to both *M. genitalium* and *M. pneumoniae* in ELISA. The arrows indicate the positions of prestained protein size markers with apparent molecular weight from top to bottom of 205 kd (kilodalton), 103 kd, 67 kd, 42 kd, 28 kd, and 18 kd, respectively.

EXAMPLE 5

Western Blot with *M. genitalium* LAMP Antigen

*M. genitalium* LAMPs (about 90 μg) prepared using the procedures taught in Example 2 were subjected to western blot analysis as taught in Example 3. The results of this analysis are shown in FIG. 5 wherein lanes A–C are sera from 3 HIV-negative individuals without positive reactivity to both *M. genitalium* and *M. pneumoniae* in ELISA, lanes D–F are sera from 3 HIV-negative individuals having positive reactivity to *M. pneumoniae* but negative reactivity to *M. genitalium* in ELISA, and lanes G–N are sera from HIV-infected patients with AIDS (G to K) and HIV-negative patients attending STD clinics (L to N) found to be positive to *M. genitalium* in ELISA. The arrows indicate the positions of prestained protein size markers with apparent molecular weight from top to bottom of 205 kd (kilodalton), 103 kd, 67 kd, 42 kd, 28 kd, and 18 kd, respectively.

EXAMPLE 6

ELISA with *M. penetrans* LAMP Antigen

*M. penetrans* TX-114 extract from Example 2 was diluted in 20 mM sodium bicarbonate buffer, pH 9.6, 0.15 M NaCl, at a protein concentration of about 2 μg/ml, and coated on Nunc-Immuno F96 MaxiSorp w/certificate plates (Nunc Inc., Naperville, Ill.) at 37° C. for 4 hours with 100 μl aliquot in each well. Followed by overcoating with 0.1% BSA plus 0.02% sodium azide at 25° C. for 2 hours and washing twice with phosphate-buffered saline (PBS), pH 7.2, plus 0.05% NP-40 (solution A), each well received 100 μl of 1:250 diluted human sera or plasma in a diluent containing 10% normal goat serum, 2% BSA, and 0.3% NP-40 in PBS. The reaction was carried out at 5° C. overnight, then at 37° C. for 90 minutes, and stopped by aspirating the excess fluid and washing the plates six times with solution A. Subsequently, each well received 100 μl of 1:1,000 diluted biotin-labeled antibody of goat anti-human IgG (r) [Kirkegaard & Perry Laboratories (kpl), Inc., Gaithersburg, Md.] in a solution containing 10% normal goat serum, 2% BSA, and 0.1% NP-40 in PBS (diluent I) incubated at 37° C. for 90 minutes, and washed as described above. Followed by incubation with 1:20,000 diluted peroxidase-labeled streptavidin (kpl) in diluent I at 37° C. for 90 minutes and washing the plates as described, each well was developed with 100 μl of ABTS peroxidase substrate solution (kpl) at 37C for 20 minutes, and the reaction was stopped by mixing with 100 μl of 1% SDS solution. The optical density at 405 nm corrected with a reference wavelength at 650 nm was measured using a microplate reader (Molecular Devices Corporation, Menlo Park, Calif.) with automatic subtraction of the OD of the blank.

The results of this analysis are shown in FIG. 1 which is a comparison of immune reactivity of *M. penetrans* antigens by ELISA in serum samples from HIV⁻normal blood donors (control), asymptomatic HIV⁺donors (AD), patients who died of "gay-related infectious disease" (GRID), patients with AIDS (AIDS), and patients attending sexually transmitted disease (STD) clinics. The number of sera tested in each group is indicated as "n=". The OD reading of 0.3 (mean value +4SD from 383 normal blood donors) was the cutoff line for this ELISA test. Each sample was tested at least twice. All positive samples were repeated three times and were also tested in plates coated with BSA without mycoplasmal antigens to rule out non-specific binding problems. The black blocks (OD $\leq 0.10$) represent 330 dots (86%) and 255 dots (76%) of samples from HIV⁻blood donors and STD clinics patients, respectively.

EXAMPLE 7

ELISA with of *M. pirum* and *M. salivarium* LAMP Antigens

*M. pirum* and *M. salivarium* LAMPs prepared using the procedures taught in Example 2 were subjected to the ELISA analysis taught in Example 6. The results of this analysis are presented in FIG. 2 which shows a comparison of antibodies to *M. pirum* and *M. salivarium* in serum samples from control subjects and from patients with AIDS. The sum of the mean value plus the value of 4 SD for sera reacting with *M. pirum* from 93 HIV⁻normal blood donors (0.296) was considered to be the cut-off for a positive result. The immune reactivity of *M. pirum* LAMP on ELISA plates was confirmed by testing with hyperimmunized rabbit antiserum which gave OD readings greater than 1.7 at 1:10000 dilution.

EXAMPLE 8

ELISA with *M. pneumoniae* LAMP Antigen

*M. pneumoniae* LAMPs prepared using the procedures taught in Example 2 were subjected to the ELISA analysis taught in Example 6. The results of this analysis are presented in FIG. 6 which shows the positive frequency for antibodies to *M. pneumoniae* LAMP antigens. The number of sera tested in each group is indicated as "n=". Control is HIV-negative healthy blood donors, AD is asymptomatic HIV-infected blood donors, AIDS is HIV⁺patients with AIDS, and STD is patients attending sexually transmitted disease clinics. The cut-off value for positivity in this ELISA was 0.45.

EXAMPLE 9

ELISA with *M. genitalium* LAMP Antigen

*M. genitalium* LAMPs prepared using the procedures taught in Example 2 were subjected to the ELISA analysis taught in Example 6. The results of this analysis are presented in FIG. 4 which shows the positive frequency of antibodies to *M. genitalium* LAMP antigens. The number of sera tested in each group is indicated as "n=". Control is HIV-negative healthy blood donors, AD is asymptomatic HIV-infected blood donors, AIDS is HIV⁺patients with AIDS, STD is patients attending sexually transmitted disease clinics, and Cancer is patients with malignant diseases (63 with various neoplasms, 81 with malignant lymphoma). The sum of the mean value plus 4 standard deviations for sera from the control subjects was used as the cut-off for positivity.

While the invention has been described in connection with specific embodiments thereof, it is understood that it is capable of further modifications. The description of the invention is intended to cover any variations, uses or adaptations of the invention following, in general, the principles of the invention, and including such departures from the present disclosure as come within known and customary practice within the art to which the invention pertains.

What is claimed is:

1. A method for detecting and differentiating polyclonal antibodies in a biological sample which are specific to at least one preselected mycoplasma species, comprising, for each preselected mycoplasma species:

(a) providing a species-specific LAMP antigen comprising a TRITON® X-114 nonionic detergent extract of lipid-associated membrane proteins (LAMP) from said preselected mycoplasma species;

(b) immobilizing said species-specific LAMP antigen on a solid phase;

(c) contacting said immobilized species-specific LAMP antigen with an aliquot of the biological sample to form solid phase immunocomplexes between said immobilized species-specific LAMP antigen and any polyclonal antibodies specific thereto in said aliquot;

(d) washing said contacted solid phase of step (c);

(e) measuring any polyclonal antibodies bound in said solid phase immunocomplexes of step (d);

(f) repeating steps (a)–(e) with an aliquot of a pooled biological sample from negative controls; and, (g) comparing the amount of bound polyclonal antibodies measured in step (e) with the amount of bound polyclonal antibodies measured in step (f), wherein said at least one predetermined mycoplasma species-specific polyclonal antibodies are present in said biological sample when the amount of bound polyclonal antibodies measured in step (e) exceeds the amount of bound polyclonal antibodies measured in step (f) by a predetermined cut-off value.

2. The method of claim 1 wherein said biological sample is a body fluid.

3. The method of claim 1 wherein said biological sample is serum.

4. The method of claim 1 wherein said biological sample is plasma.

5. The method of claim 1 wherein said at least one preselected mycoplasma species is selected from the group consisting of *M. penetrans*, *M. fermentans*, *M. orale*, *M. pirum*, *M. pneumoniae*, *M. genitalium*, *M. salivarium*, *M. hominis*, *Acholeplasma laidlawaii* and combinations thereof.

6. The method of claim 5 wherein said at least one preselected mycoplasma species is selected from the group consisting of *M. penetrans*, *M. pirum*, *M. pneumoniae*, *M. genitalium*, *M. salivarium* and combinations thereof.

7. A diagnostic assay for detecting and differentiating infection in a test subject by at least one preselected mycoplasma species, comprising, for each preselected mycoplasma species:

(a) providing a species-specific LAMP antigen comprising a TRITON® X-114 nonionic detergent extract of lipid-associated membrane proteins (LAMP) from said preselected mycoplasma species;

(b) immobilizing said species-specific LAMP antigen on a solid phase;

(c) contacting said immobilized species-specific LAMP antigen with an aliquot of the biological sample from said test subject to form solid phase immunocomplexes between said immobilized species-specific LAMP antigen and any polyclonal antibodies specific thereto in said aliquot;

(d) washing said contacted solid phase of step (c);

(e) measuring any polyclonal antibodies bound in said solid phase immunocomplexes of step (d);

(f) repeating steps (a)–(e) with an aliquot of a pooled biological sample from control subjects free of past or present mycoplasma infection;

(g) comparing the amount of bound polyclonal antibodies measured in step (e) with the amount of bound polyclonal antibodies measured in step (f), wherein said at least one predetermined mycoplasma species-specific polyclonal antibodies are present in said biological sample from said test subject when the amount of bound polyclonal antibodies measured in step (e) exceeds the amount of bound polyclonal antibodies measured in step (f) by a predetermined cut-off value; and, (h) identifying the presence of infection in said test subject caused by said at least one preselected mycoplasma based upon the presence of polyclonal antibodies specific to said predetermined mycoplasma species in said biological sample from said test subject.

8. The assay of claim 7 wherein said biological sample is a body fluid.

9. The assay of claim 7 wherein said biological sample is serum.

10. The assay of claim 7 wherein said biological sample is plasma.

11. The assay of claim 7 wherein said at least one preselected mycoplasma species is selected from the group consisting of *M. penetrans, M. fermentans, M. orale, M. pirum, M. pneumoniae, M. genitalium, M. salivarium, M. hominis, Acholeplasma laidawaii* and combinations thereof.

12. The assay of claim 11 wherein said at least one preselected mycoplasma species is selected from the group consisting of *M. penetrans, M. pirum, M. pneumoniae, M. genitalium, M. salivarium* and combinations thereof.

* * * * *